United States Patent
Keilman et al.

(10) Patent No.: US 8,128,566 B2
(45) Date of Patent: Mar. 6, 2012

(54) ENHANCED INTRALUMINAL FLOW MEASUREMENT METHOD USING PULSED SIGNALS

(75) Inventors: George W. Keilman, Bothell, WA (US); Leigh Bartlett, Bothell, WA (US); Timothy Johnson, Bothell, WA (US)

(73) Assignee: Pacesetter, Inc., Sylmar, CA (US)

( * ) Notice: Subject to any disclaimer, the term of this patent is extended or adjusted under 35 U.S.C. 154(b) by 993 days.

(21) Appl. No.: 12/105,050

(22) Filed: Apr. 17, 2008

(65) Prior Publication Data

US 2009/0264763 A1  Oct. 22, 2009

(51) Int. Cl.
*A61B 8/06* (2006.01)
(52) U.S. Cl. ...................................................... 600/454
(58) Field of Classification Search .................. 600/454, 600/438
See application file for complete search history.

(56) References Cited

U.S. PATENT DOCUMENTS

| 4,556,063 A | * | 12/1985 | Thompson et al. | ............ 607/32 |
| 6,626,838 B2 | * | 9/2003 | Doten et al. | ................. 600/465 |

* cited by examiner

*Primary Examiner* — Jacqueline Cheng

(57) ABSTRACT

An enhanced intraluminal flow measurement system and method is conducive for a low-power ultrasonic system that can use continuous-wave (CW) Doppler sensing and wireless RF telemetry. Applications include measurement of blood flow in situ in living organisms. Implementations include an extraluminal component located outside of a body, such as a human or animal body, containing a lumen. The extraluminal component can be wirelessly coupled via an RF magnetic field or other RF field to an implantable intraluminal component. The intraluminal component (i.e. implant) is implanted inside of the lumen of the body such as a heart or elsewhere in a vasculature (such as in a dialysis shunt). The intraluminal component can telemeter, via RF electromagnetic signals, flow data directly out of the body housing the intraluminal component to be received by the extraluminal component.

24 Claims, 10 Drawing Sheets

ENHANCED INTRALUMINAL FLOW MEASUREMENT METHOD USING PULSED SIGNALS

BACKGROUND OF THE INVENTION

1. Field of the Invention

The present invention is generally related to flow measurement.

2. Description of the Related Art

Conventional methods for measuring intraluminal flow, such as blood flow, include use of continuous wave Doppler methods in which a transducer transmits an ultrasonic signal and another transducer receives echoes from the sound reflecting off of surfaces moving along with the fluid. These conventional systems are generally more responsive to a velocity component of the flow that is along a midline between the two transducers.

Conventional approaches include a first intraluminal transducer configuration 10, which positions a transmit transducer 12 and a receive transducer 14 on opposite sides of a lumen 16 (such as in an inner area of a blood vessel or other biological structure of a biological body) as shown in FIG. 1. With these conventional approaches the transmit transducer 12 and the receive transducer 14 are symmetrically aligned with a first fluid flow 18a and/or an oppositely directed second fluid flow 18b, which both collective are known herein as fluid flow 18. The transmit transducer 12 sends out a transmitted beam 19 that is reflected off of surfaces 20 traveling in the first fluid flow 18a and/or the second fluid flow 18b through a sampling region 22 as a reflected beam 24 to be received by the receive transducer 14.

Alignment of the transmit transducer 12 and the receive transducer 14 is such that the transmitted beam 19 and the reflected beam 24 are downstream of the transducers with respect to the first fluid flow 16 and upstream of the transducers with respect to the second fluid flow 18 as further shown in FIG. 1. By symmetrically positioning the transmit transducer 12 and the receive transducer 14 in the lumen, measurements can be responsive to a flow vector component that is coaxial with an overall longitudinal direction 26 of the lumen to increase sensitivity of the flow measurement.

Other conventional approaches include a second intraluminal transducer configuration 30 that positions the transmit transducer 12 and the receive transducer 14 on a same side of the lumen 16 as shown in FIG. 2. In implementations, the transmitted beam 19 and the reflected beam 24 are obliquely aimed to overlap into a version of the sampling region 22 that can have a trapezoidal shape.

Unfortunately, in at least some cases, space to position fluid flow measuring devices intraluminally is rather limited, which tends to restrict the number and/or quality of the device components used. Consequently, measurement accuracy of fluid flow may be less than desirable.

BRIEF DESCRIPTION OF THE SEVERAL VIEWS OF THE DRAWING(S)

DETAILED DESCRIPTION OF THE INVENTION

As discussed herein, implementations of an enhanced intraluminal flow measurement system and method is conducive for a low-power ultrasonic system that can use continuous-wave (CW) Doppler sensing and wireless RF telemetry. Applications include measurement of blood flow in situ in living organisms. Implementations include an extraluminal component located outside of a body, such as a human or animal body, containing a lumen. The extraluminal component can be wirelessly coupled via an RF magnetic field or other RF field to an implantable intraluminal component. The intraluminal component (i.e. implant) is implanted inside of the lumen of the body such as a heart or elsewhere in a vasculature (such as in a dialysis shunt). The intraluminal component can telemeter, via RF electromagnetic signals, flow data directly out of the body housing the intraluminal component to be received by the extraluminal component.

The implementations can allow a reduced number of electrical circuit components having electrical power and space requirements more conducive for insertion inside areas sized such as having a typical intravascular or intracardiac catheter diameter. Low power requirements can promote a wider selection of power delivery alternatives. Consequently, continuous, real-time interrogation of fluid flow velocity using ultrasonic transducers is more readily available. Some implementations can be placed in intravascular locations in animals or in the human body for the purpose of measuring blood flow.

With some implementations a 1st signal representing a Doppler shift due to fluid flow and a 2nd signal associated with an oscillator reference oscillator can be simultaneously transmitted out of the body without interfering with each other. With this approach complex (two-sided) Doppler spectrum is preserved to provide directional information regarding the flow. Alternative implementations transmit a baseband Doppler signal out of the body by modulating an RF carrier to provide a one-sided Doppler spectrum with no direction information.

Implementations can be configured to sense fluid flow velocity, such as average velocity, without requiring precise aiming of an external data collection device found with conventional approaches to increase availability for use in non-specialist clinics or in homes. Furthermore, fluid flow parameters can be automatically sampled periodically over an extended period of time in a fixed location within a predetermined distance from the subject. Alternatively, fluid flow parameters can be continuously sampled to provide trending data. Additionally, instantaneous fluid flow velocity can be sampled rapidly, to provide a flow velocity waveform, in a non-specialist environment.

Figure 1:
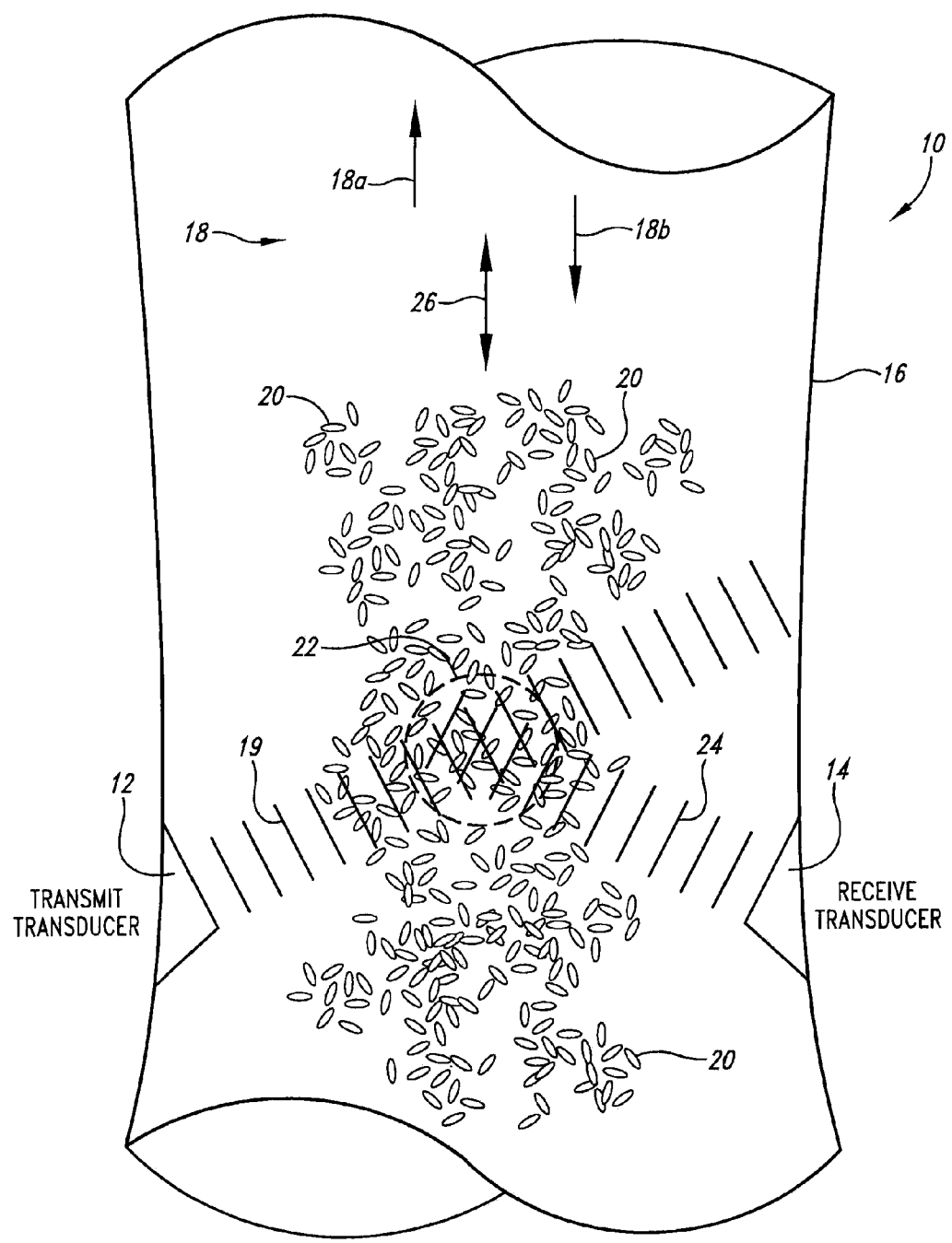
FIG. 1 is a sectional view of a first conventional positioning of a transmit transducers and a receive transducer for measuring intraluminal fluid flow.
Figure 2:
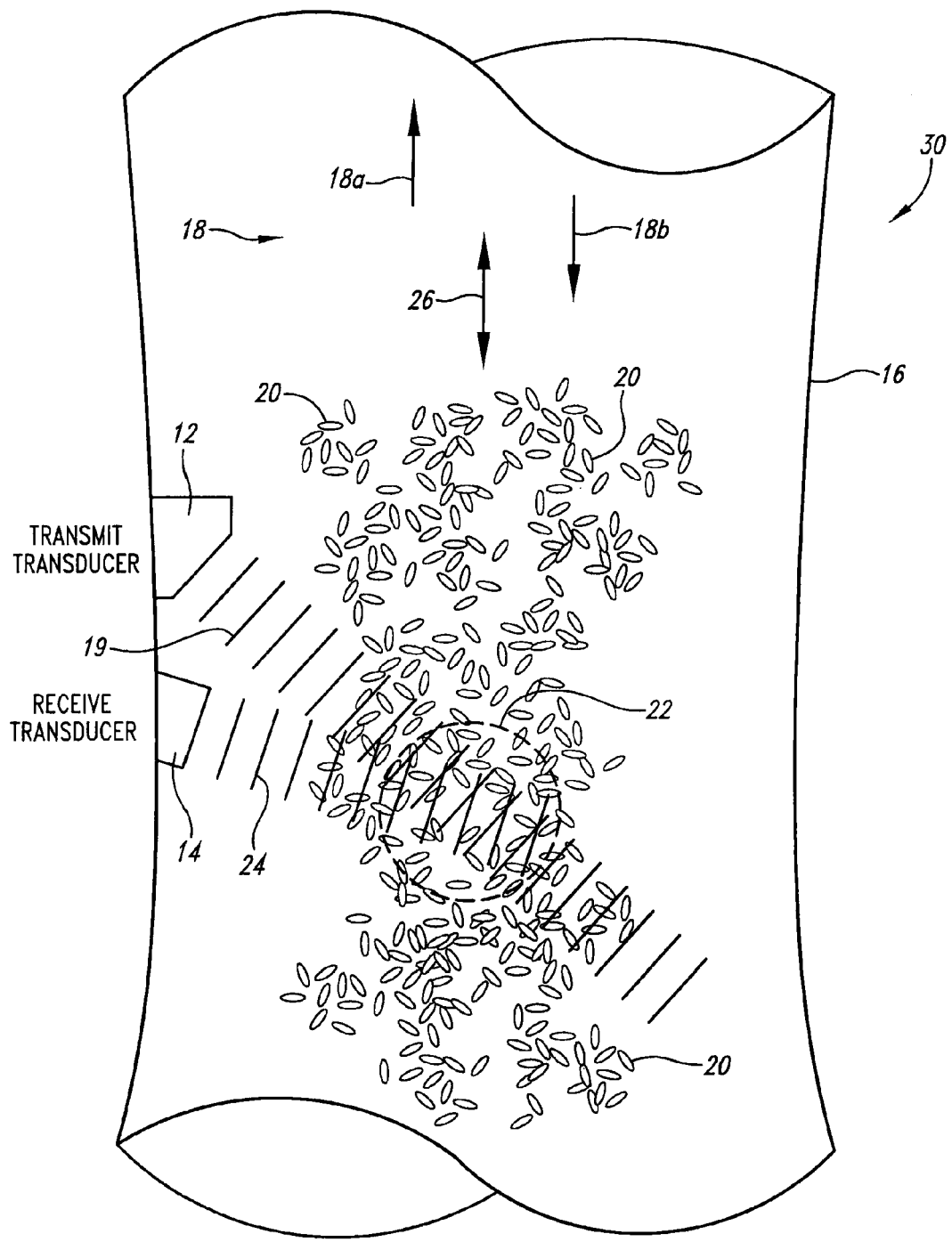
FIG. 2 is a sectional view of a second conventional positioning of a transmit transducer and a receive transducer for measuring intraluminal fluid flow.
Figure 3:
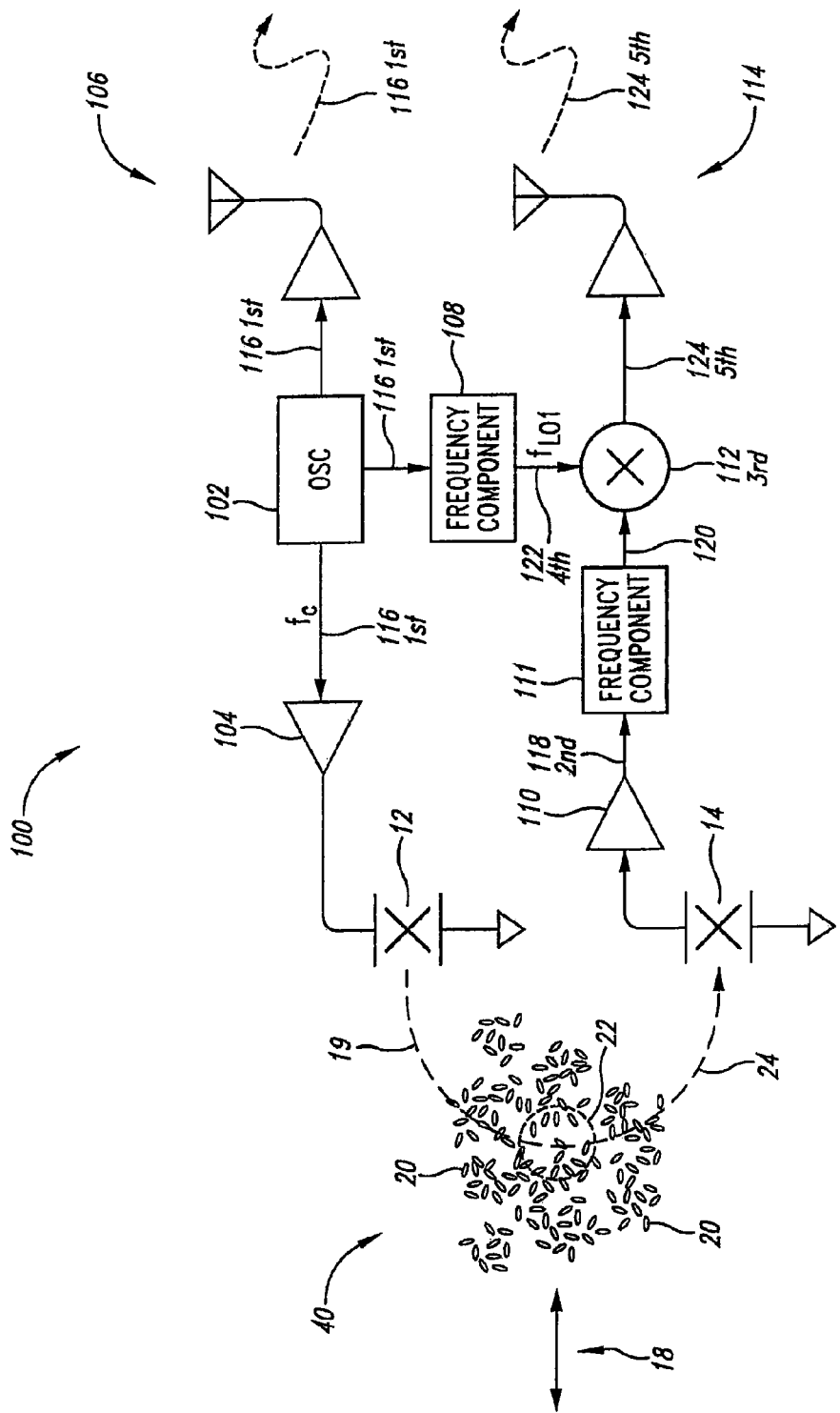
FIG. 3 is a schematic block diagram of an intraluminal component of a first version of an enhanced intraluminal flow measurement system.

An intraluminal component 100 of a first version of an enhanced intraluminal flow measurement system is shown in FIG. 3 as having an oscillator 102, an amplifier 104, an antenna-amplifier transmitter unit 106, a frequency-selective filter 108, an amplifier 110, a frequency-selective filter 111, a mixer 112, and an antenna-amplifier transmitter unit 114. In some implementations, the antenna-amplifier transmitter unit 106 and the antenna-amplifier transmitter unit 114 can be part of a single transmitter assembly. The oscillator 102 generates the 1st signal 116 having a depicted frequency, $f_C$. The 1st signal is transmitted by the transmitter unit 106 to be received outside a body containing the lumen 16. The 1st signal 116 is also amplified by the amplifier 104 and sent by the transmit transducer 12 as an ultrasonic signal into the fluid flow 18 to be reflected off of surfaces 20 in the sampling region or area 22 as the reflected beam 24 to be received by the receive transducer 14 and passed as an electrical signal to the amplifier 110 and outputted as a 2nd signal 118. As a result of reflection of the 1st signal 116 off of the surfaces 20, the frequency of the 2nd signal 118 is a Doppler shifted (either up-shifted or down-shifted) version of the frequency of the 1st signal depending upon direction of the fluid flow 18 and placement of the transmit transducer 12 and the receive transducer 14.

If the sampling region 22 is upstream of the transmit transducer 12 and the receive transducer 14, then the frequency of the 2nd signal 118 will be Doppler up-shifted as the frequency of the 1st signal, $f_C$, plus a Doppler frequency shift, dF, according to principles of Doppler physics. If the sampling region 22 is downstream of the transmit transducer 12 and the receive transducer 14, then the frequency of the 2nd signal will be Doppler down-shifted as the frequency of the 1st signal, $f_C$, minus the Doppler frequency shift, dF, according to principles of Doppler physics. The transmit transducer 12 and the receive transducer 14 are depicted in FIG. 3 as being in a generalized configuration 40 that represents both instances in which the first intraluminal transducer configuration 10 is used and also represents instances in which the second intraluminal transducer configuration 30 is used.

The 2nd signal 118 is inputted into the frequency-selective filter 111 and outputted as the 3rd signal 120 being selectively filtered having a frequency with a numerical fraction or numerical multiple of the frequency of the 2nd signal. The frequency-selective filter 111 serves as a pass-through so that the frequency of the 3rd signal 120 can be the same as the frequency of the 2nd signal 118. The oscillator 102 also sends the 1st signal 116 to the frequency-selective filter 108, which outputs a 4th signal 122 having a frequency with a numerical fraction or numerical multiple of the frequency of the 1st signal. In some implementations, the frequency-selective filter 108 serves as a pass-through so that the frequency of the 4th signal 122 can be the same as the frequency of the 1st signal 116. The mixer 112 combines the 3rd signal 120 and the 4th signal 122 to output a 5th signal 124. In some implementations, the 5th signal 124 is a linear combination of the 3rd signal 120 and the 4th signal 122 whereas in other combinations the 5th signal is a non-linear combination of the 3rd signal 120 and the 4th signal 122.

The 5th signal 124 is transmitted by the transmitter unit 114 to be received outside the body containing the lumen 16. In some implementations, the frequency-selective filter 108 acts as a frequency divider to divide the frequency of the 1st signal 116, the implant's local oscillator frequency, $f_C$, by an integer N to produce the 4th signal 122, which is mixed with the 3rd signal 120 by the mixer 112 to be transmitted as the 5th signal 124 by the transmitter unit 114.

Figure 4A:
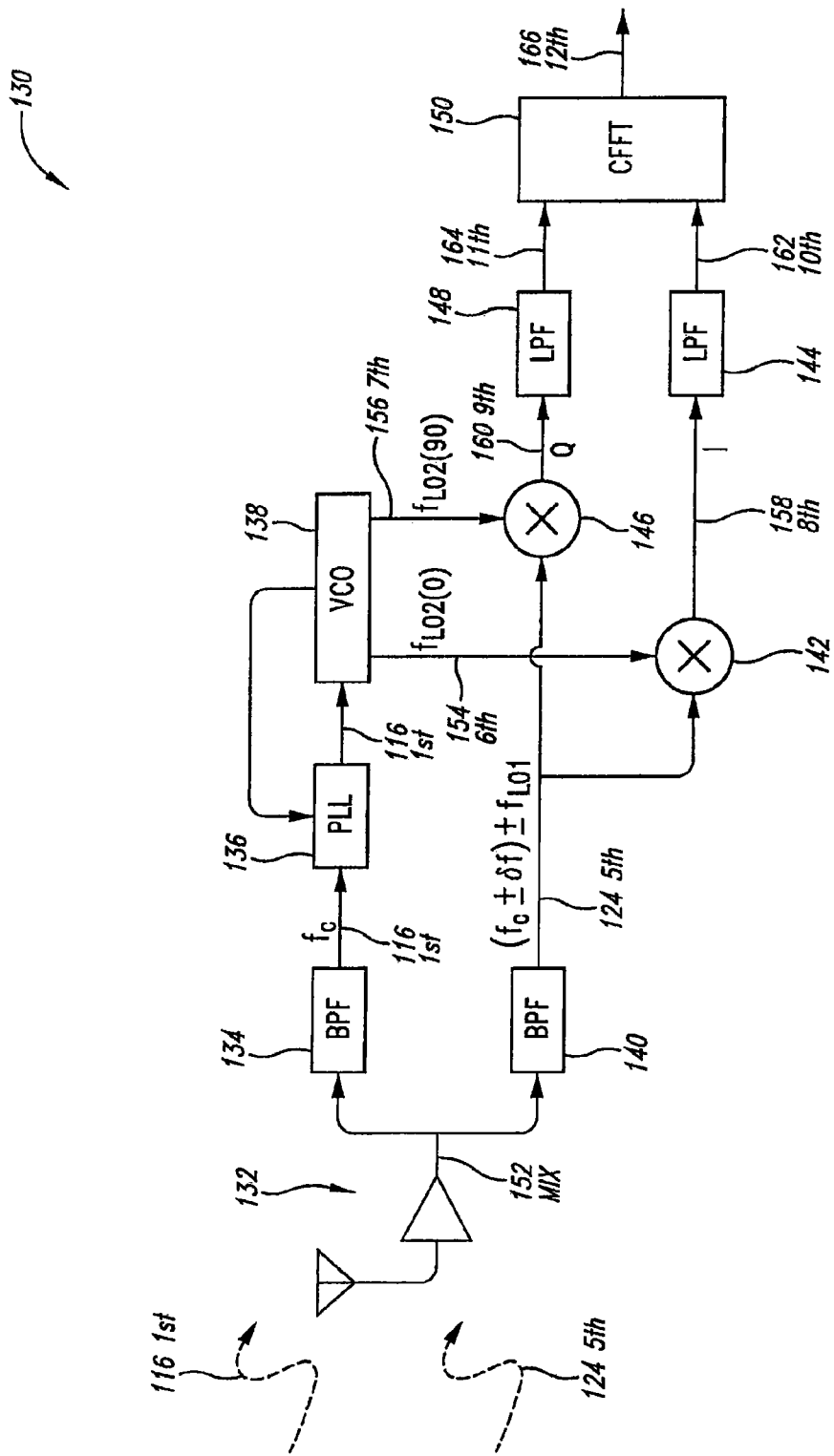
FIG. 4A is a schematic block diagram of a first extraluminal component implementation of the first version of enhanced intraluminal flow measurement system.

A first extraluminal component implementation 130 of the first version of the enhanced intraluminal flow measurement system is shown in FIG. 4A as having an antenna-amplifier receiver unit 132, a bandpass filter 134, a phase-lock loop 136, the voltage controlled oscillator (VCO) 138, a bandpass filter 140, a mixer 142, a low-pass filter 144, a mixer 146, a low-pass filter 148, and a frequency transformation module 150. Examples of suitable frequency transformations include discrete Fourier transforms, real and complex fast Fourier transforms (FFT), fast Hartley transforms, and related transforms and spectral estimators. The real transforms provide only the single-sided spectrum, whereas the complex transforms provide the two-sided spectrum needed for directional flow measurement in situations where the flow can be in either direction. In some implementations the antenna-amplifier receiver unit 132, the bandpass filter 134 and the bandpass filter 140 can be part of a single receiver assembly. The 1st signal 116 from the transmitter unit 106 and the 5th signal 124 from the transmitter unit 114 are received by the receiver unit 132 and passed on as a combined signal 152. The bandpass filter 134 selects the 1st signal 116 out from the combined signal 152 to pass on the 1st signal to the phase-lock loop 136.

The phase-lock loop 136 locks onto the 1st signal 116, which controls the VCO 138 in generating a 6th signal 154, which is an in-phase (0°) difference of the 4th signal 122 subtracted from the 1st signal 116 and in generating a 7th signal 156, which is a quadrature (90°) difference of the 4th signal subtracted from the 1st signal. The mixer 142 combines the 5th signal 124 with the 6th signal 154 to produce the 8th signal 158. The mixer 146 combines the 5th signal 124 with the 7th signal 156 to produce the 9th signal 160. The low-pass filter 144 attenuates the 8th signal 158 to produce the 10th signal 162.

The low-pass filter 148 attenuates the 9th signal 160 to produce the 11th signal 164. The 10th signal 162 and the 11th signal 164 are digitized and fed into the frequency transformation module 150, which transforms the signals from the time domain to the frequency domain. This results in a 12th signal 166 having a complex, two-sided Doppler spectrum with accompanying two-sided axis, that discriminates between the two types of flow velocities (flow toward and flow away from the receive transducer 14) by placing each type on either side of the two-sided axis. Consequently, separation in measurement of these forward and reverse flows can be accomplished.

Figure 4B:
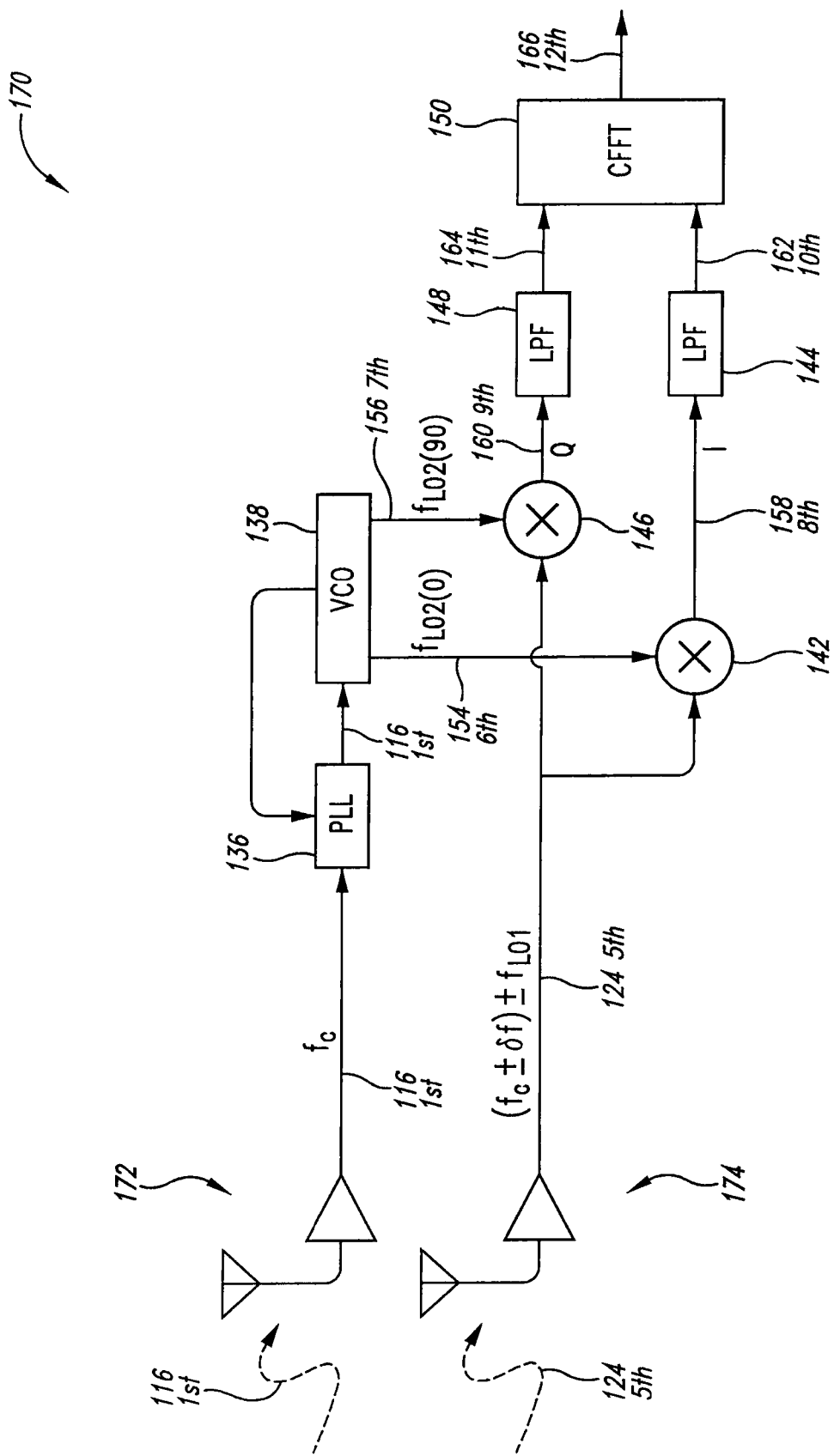
FIG. 4B is a schematic block diagram of a second extraluminal component implementation of the first version of the enhanced intraluminal flow measurement system.

A second extraluminal component implementation 170 of the first version of the enhanced intraluminal flow measurement system is shown in FIG. 4B as having an antenna-amplifier receiver unit 172 that passes the 1st signal 116 from the transmitter unit 106 on to the phase-lock loop 136 and an antenna-amplifier receiver unit 174 that passes the 5th signal 124 from the transmitter unit 114 on to the mixer 142 and the mixer 146. In some implementations the antenna-amplifier receiver unit 172 and the antenna-amplifier receiver unit 174 can be part of a single receiver unit.

Figure 5:
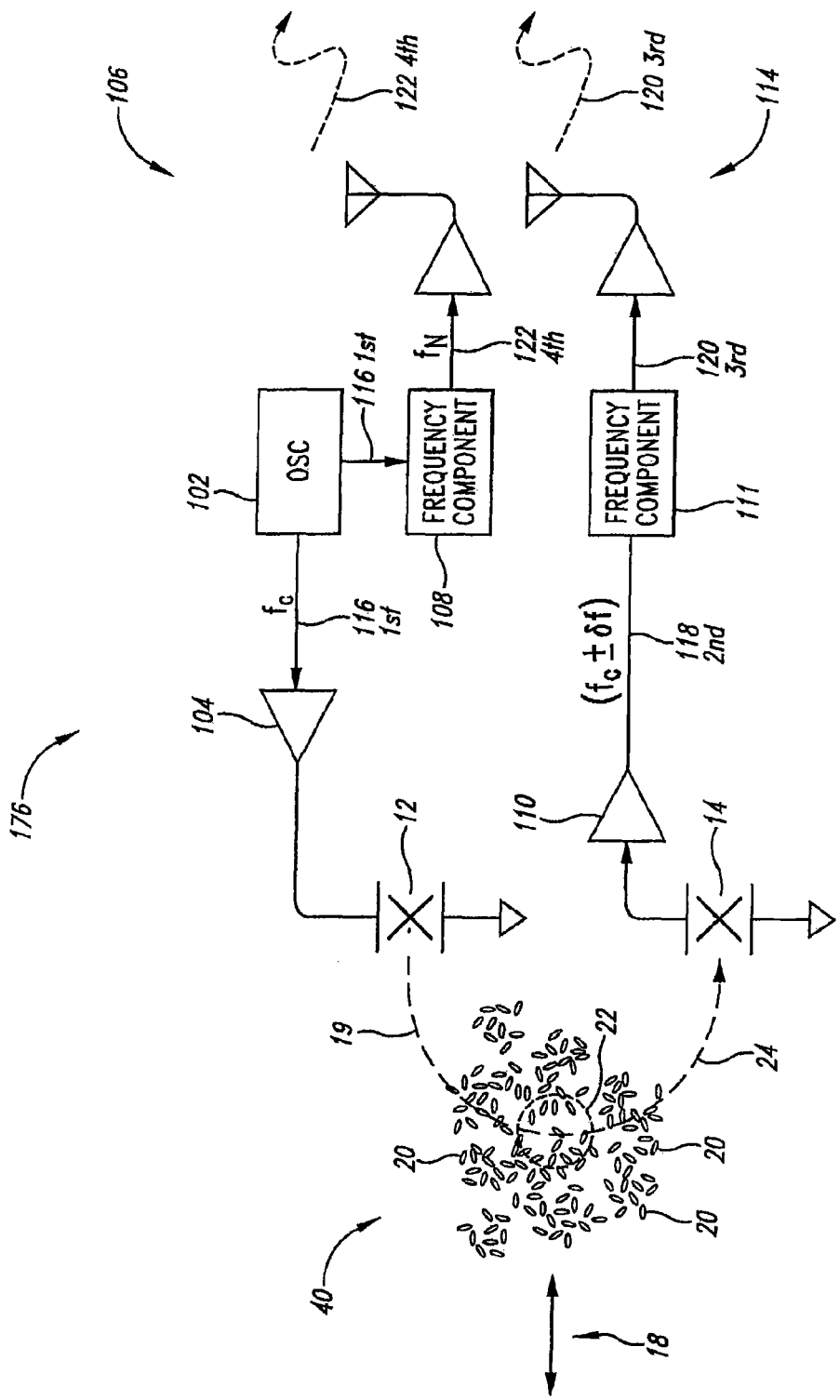
FIG. 5 is a schematic block diagram of an intraluminal component implementation of a second version of the enhanced intraluminal flow measurement system.

An intraluminal component 176 of a second version of the enhanced intraluminal flow measurement system is shown in FIG. 5 as having the frequency-selective filter 108 coupled to the transmitter unit 106 to send the 4th signal 122 outside of the lumen 16. For the intraluminal component 176, the frequency-selective filter 111 is coupled to the transmitter unit 114 to send the third signal 120 outside of the lumen 16. In implementations where the frequency-selective filter 111 is a pass-through, either the amplifier 110 or the amplifier of the transmitter unit 114 need not be present.

Figure 6A:
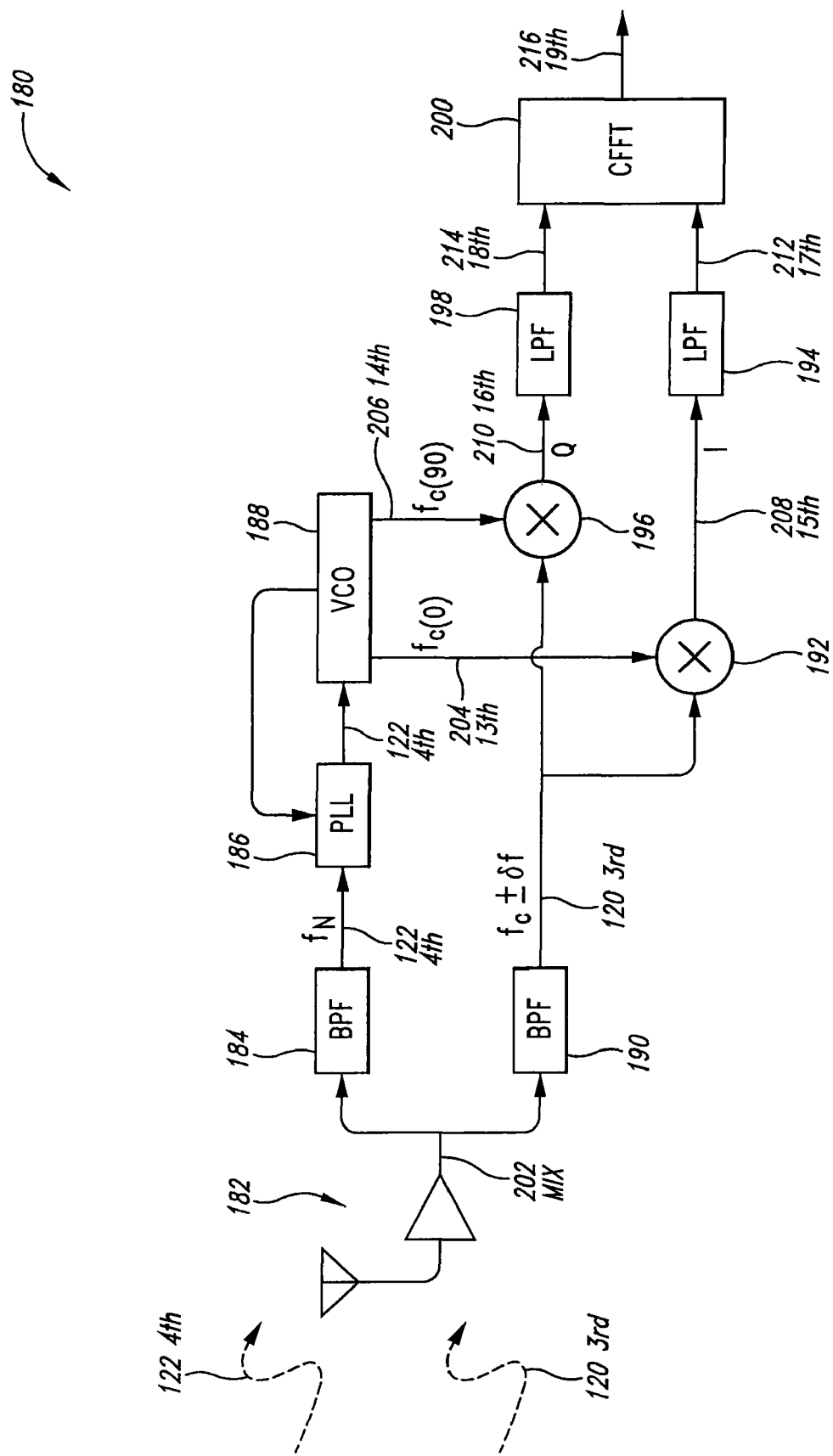
FIG. 6A is a schematic block diagram of a first extraluminal component implementation of the second version of the enhanced intraluminal flow measurement system.

A first extraluminal component implementation 180 of a second version of the enhanced intraluminal flow measurement system is shown in FIG. 6A as having an antenna-amplifier receiver unit 182, a bandpass filter 184, a phase-lock loop 186, the VCO 188, a bandpass filter 190, a mixer 192, a low-pass filter 194, a mixer 196, a low-pass filter 198, and a frequency transformation module 200. Examples of suitable frequency transformations include discrete Fourier transforms, real and complex fast Fourier transforms (FFT), fast Hartley transforms, and related transforms and spectral estimators. The real transforms provide only the single-sided spectrum, whereas the complex transforms provide the two-sided spectrum needed for directional flow measurement in situations where the flow can be in either direction. In some implementations, the antenna-amplifier receiver unit 182, the bandpass filter 184, and the bandpass filter 190 can be a single receiver assembly. The 4th signal 122 from the transmitter unit 106 and the 3rd signal 120 from the transmitter unit 114 are received by the receiver unit 182 and passed on as a combined signal 202. The bandpass filter 184 selects the 4th signal 122 out from the combined signal 202 to pass on the 4th signal to the phase-lock loop 186.

The phase-lock loop 186 locks onto the 4th signal 122, which controls the VCO 188 in generating a 13th signal 204, which is an in-phase (0°) or cosine version of the first signal 116 and in generating a 14th signal 206, which is a quadrature (90°) or sine version of the first signal 116. The mixer 192 combines the 3rd signal 120 with the 13th signal 204 to produce the 15th signal 208. The mixer 196 combines the 3rd signal 120 with the 14th signal 206 to produce the 16th signal 210. The low-pass filter 194 attenuates the 15th signal 208 to produce the 17th signal 212.

The low-pass filter 198 attenuates the 16th signal 210 to produce the 18th signal 214. The 17th signal 212 and the 18th signal 214 are digitized and fed into the frequency transformation module 200, which transforms the signals from the time domain to the frequency domain. This results in a 19th signal 216 having a complex, two-sided Doppler spectrum with accompanying two-sided axis, that discriminates between the two types of flow velocities (flow toward and flow away from the receive transducer 14) by placing each type on either side of the two-sided axis. Consequently, separation in measurement of these forward and reverse flows can be accomplished.

Figure 6B:
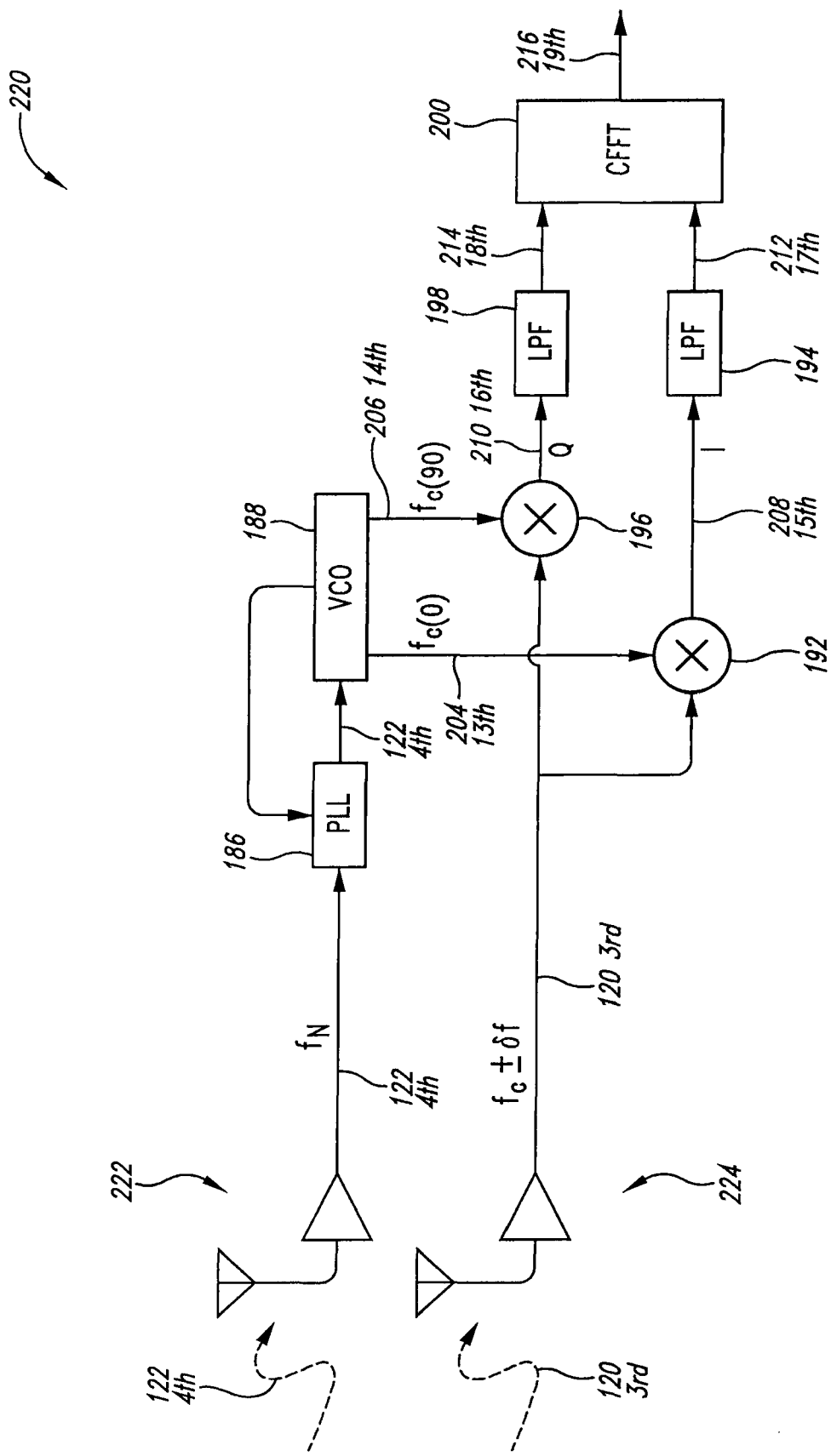
FIG. 6B is a schematic block diagram of a second extraluminal component implementation of the second version of the enhanced intraluminal flow measurement system.

A second extraluminal component implementation 220 of the second version of the enhanced intraluminal flow measurement system is shown in FIG. 6B as having an antenna-amplifier receiver unit 222 that passes the 4th signal 122 from the transmitter unit 106 on to the phase-lock loop 186 and an antenna-amplifier receiver unit 224 that passes the 3rd signal 120 from the transmitter unit 114 on to the mixer 192 and the mixer 196. In some implementations, the antenna-amplifier receiver unit 222 and the antenna-amplifier receiver unit 224 can be a single receiver assembly.

Figure 7:
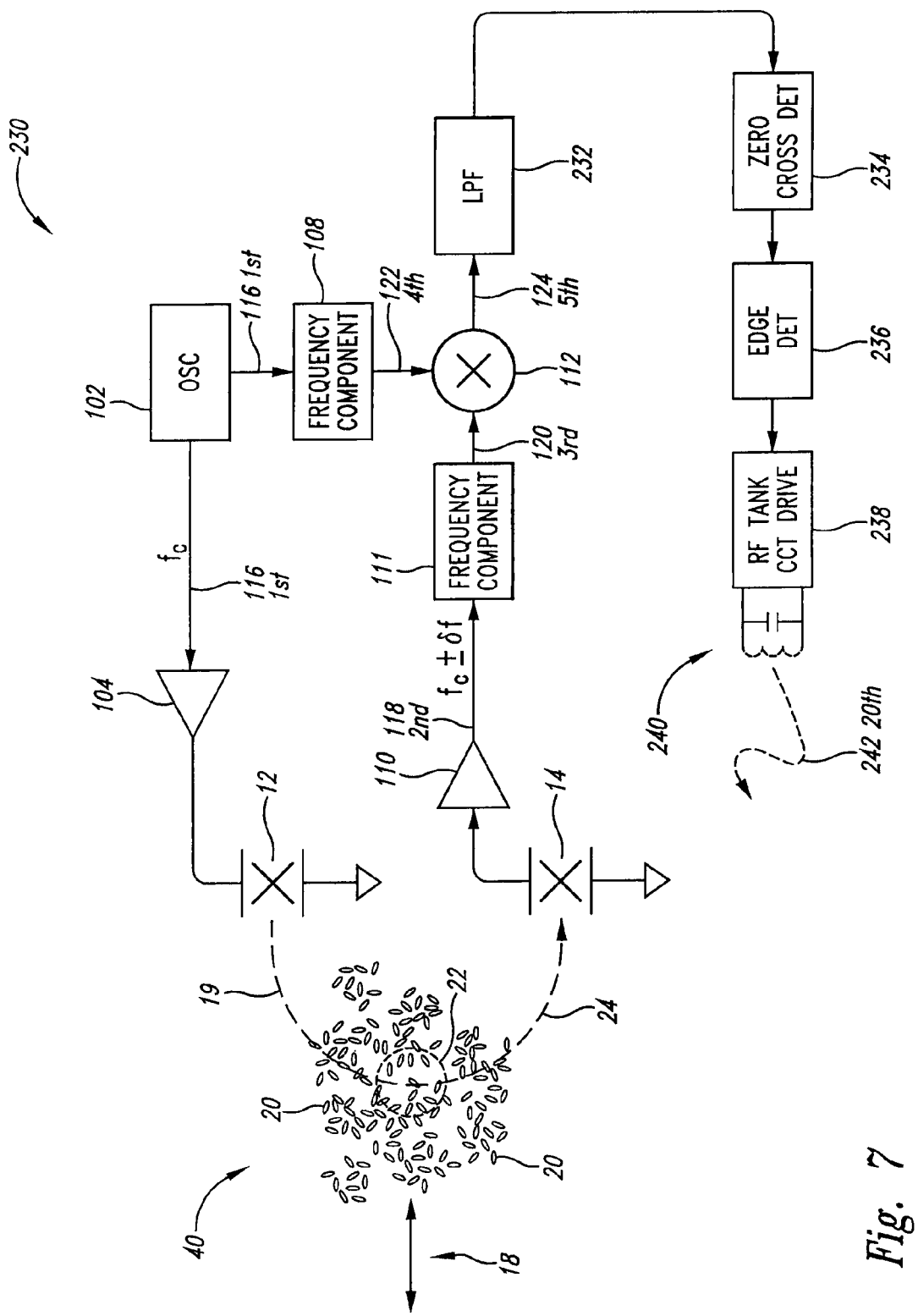
FIG. 7 is a schematic block diagram of an intraluminal component implementation of a third version of the enhanced intraluminal flow measurement system.

An intraluminal component 230 of a third version of the enhanced intraluminal flow measurement system is shown in FIG. 7 as including low-pass filter 232, a zero cross detector 234, an edge detector 236, an RF tank circuit 238, and a transmitter unit 240. The intraluminal component 230 sends the fifth signal 124 from the mixer 112 to the low-pass filter 232 to attenuate the sum-frequency-selective filters from the mixer and is passed on to the zero cross detector 234 and then on to the edge detector 236 to produce edge events. The edge events are used to trigger bursts of RF oscillation in the RF tank circuit 238, which is connected to the transmitter unit or assembly 240, which transmits a 20th signal 242 outside the lumen 16.

Figure 8:
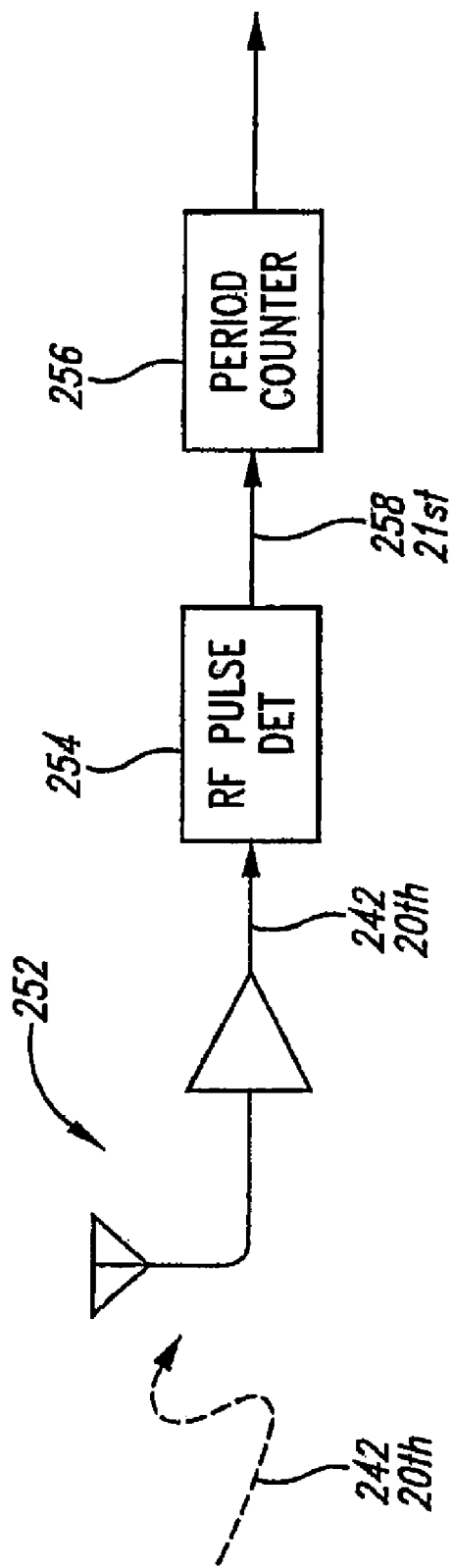
FIG. 8 is a schematic block diagram of an extraluminal component implementation of the third version of the enhanced intraluminal flow measurement system.

An extraluminal component implementation of the third version of the enhanced intraluminal flow measurement system is shown in FIG. 8 as having an antenna-amplifier receiver unit 252, an RF pulse detector 254, and a period counter 256. The receiver unit or assembly 252 receives the 20th signal 242, which is passed on to the RF pulse detector 254 that sends detected RF pulses contained in the 20th signal as a 21st signal. The period counter 256 measures the time intervals between the pulses of the 21st signal 258 and outputs a measure of the mean frequency of the second signal 118, which is the Doppler signal.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. For an implant for implantation into a biological structure having a fluid flow of an average velocity with surfaces traveling with substantially the average velocity in the fluid flow through the biological structure, a method comprising:
generating a first electrical signal having a first frequency;
transmitting an acoustic beam based upon the first electrical signal into the fluid flow;
receiving a reflected portion of the acoustic beam reflected off of a portion of the surfaces traveling in the fluid flow;
producing a second electrical signal based upon the portion of the acoustic beam;
receiving a third electrical signal based upon the second electrical signal;
receiving a fourth electrical signal based upon the first electrical signal;
outputting a mixed fifth electrical signal based upon the third electrical signal and the fourth electrical signal;
receiving triggering events based upon the fifth signal;
generating bursts of RF oscillation based upon the received triggering events; and
transmitting an electromagnetic signal containing pulses based upon the bursts of RF oscillation and transmitting an unmixed electromagnetic signal based on the first electrical signal.

2. The method of claim 1, further including attenuating sum-frequency components from the fifth electrical signal.

3. The method of claim 1, further including outputting edge events as the triggering events.

4. The method of claim 1 wherein the fourth signal has a frequency substantially a multiple of the frequency of the first signal.

5. The method of claim 4 wherein the fourth signal has a frequency substantially an integer multiple of the frequency of the first signal.

6. The method of claim 1 wherein the fourth signal has a frequency substantially a fraction of the frequency of the first signal.

7. The method of claim 6 wherein the fourth signal has a frequency substantially an integer fraction of the frequency of the first signal.

8. The method of claim 1 wherein the reflected portion of the acoustic beam has substantially the same frequency of the first electrical signal Doppler shifted according to the average velocity of the fluid flow.

9. The method of claim 1 wherein the third signal has a frequency substantially a multiple of the frequency of the second signal.

10. The method of claim 9 wherein the third signal has a frequency substantially an integer multiple of the frequency of the second signal.

11. The method of claim 1 wherein the third signal has a frequency substantially a fraction of the frequency of the second signal.

12. The method of claim 11 wherein the third signal has a frequency substantially an integer fraction of the frequency of the second signal.

13. The method of claim 1 wherein the transmitted acoustic beam has substantially the same frequency as the first electrical signal.

14. A method comprising:
for a location in a biological structure of a biological body having a fluid flow of an average velocity with surfaces traveling with substantially the average velocity in the fluid flow through the biological structure, performing the following:
generating a first electrical signal having a first frequency;
outputting a combined electrical signal of a related version of the first electrical signal having a selectively filtered frequency of the first frequency and a related version of a second electrical signal having a selectively filtered frequency of the second electrical signal, the second electrical signal having substantially the frequency of the first electrical signal Doppler shifted according to the average velocity in the fluid flow; and
transmitting an electromagnetic signal containing pulses associated with the Doppler shift of the first frequency found in the second electrical signal and transmitting an unmixed electromagnetic signal based on the first electrical signal; and
for a location outside of the biological body, performing the following:
receiving the electromagnetic signal and the unmixed electromagnetic signal; and
outputting in an electrical signal the pulses contained in the electromagnetic signal.

15. The method of claim 14, for the location outside of the biological body, further including detecting the pulses outputted by the receiver.

16. The method of claim 15, for the location outside of the biological body, further including measuring the time intervals between the detected pulses.

17. The method of claim 15, for the location outside of the biological body, further including outputting a mean frequency indicative of the related version of the second electrical signal thereby indicating extent of Doppler shifting of the first electrical signal according to the average velocity of the fluid flow.

18. The method of claim 14, for the location in the biological structure, further including:
receiving triggering events based upon the combined signal outputted from a mixer;
generating bursts of RF oscillation based upon the triggering events, the generated bursts of RF oscillation to substantially become the pulses contained in the electromagnetic signal.

19. The method of claim 14 wherein the selectively filtered frequency of the first frequency is substantially the first frequency.

20. The method of claim 14 wherein the selectively filtered frequency of the first frequency is substantially a multiple of the first frequency.

21. The method of claim 14 wherein the selectively filtered frequency of the first frequency is substantially a fraction of the first frequency.

22. The method of claim 14 wherein the selectively filtered frequency of the second frequency is substantially the second frequency.

23. The method of claim 14 wherein the selectively filtered frequency of the second frequency is substantially a multiple of the second frequency.

24. The method of claim 14 wherein the selectively filtered frequency of the second frequency is substantially a fraction of the second frequency.

* * * * *